(12) United States Patent
Emonds et al.

(10) Patent No.: US 9,139,540 B1
(45) Date of Patent: Sep. 22, 2015

(54) METHOD FOR PREPARATION OF 2-ALKYL-1,2-BENZISOTHIAZOLIN-3-ONES

(71) Applicants: Rohm and Haas Company, Philadelphia, PA (US); Dow Global Technologies LLC, Midland, MI (US)

(72) Inventors: Mark V. M. Emonds, Indianapolis, IN (US); Daniel R. Henton, Midland, MI (US); Randall W. Stephens, Perkasie, PA (US)

(73) Assignees: Dow Global Technologies LLC, Midland, MI (US); Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 14/441,875

(22) PCT Filed: Nov. 19, 2013

(86) PCT No.: PCT/US2013/070740
§ 371 (c)(1),
(2) Date: May 11, 2015

(87) PCT Pub. No.: WO2014/085138
PCT Pub. Date: Jun. 5, 2014

Related U.S. Application Data

(60) Provisional application No. 61/730,700, filed on Nov. 28, 2012.

(51) Int. Cl.
*C07D 275/04* (2006.01)

(52) U.S. Cl.
CPC .................................. *C07D 275/04* (2013.01)

(58) Field of Classification Search
USPC ........................................................ 548/209
See application file for complete search history.

(56) References Cited

U.S. PATENT DOCUMENTS

| | | | |
|---|---|---|---|
| 4,293,702 A | 10/1981 | Umemura et al. | |
| 5,594,018 A | 1/1997 | Austin | |

FOREIGN PATENT DOCUMENTS

JP    1996277278    10/1996

OTHER PUBLICATIONS

Chem. Ber., (1928), vol. 61, pp. 1308-1316.

*Primary Examiner* — Laura L. Stockton
(74) *Attorney, Agent, or Firm* — Kenneth Crimaldi

(57) ABSTRACT

A method for preparation of 2-alkyl-1,2-benzisothiazolin-3-ones from 1,2-benzisothiazolin-3-one by contacting 1,2-benzisothiazolm-3-one with a dialkyl carbonate in the presence of a base.

10 Claims, No Drawings

METHOD FOR PREPARATION OF 2-ALKYL-1,2-BENZISOTHIAZOLIN-3-ONES

This invention relates to a method for preparation of 2-alkyl-1,2-benzisothiazolin-3-ones from 1,2-benzisothiazolin-3-one.

Alkylation of 1,2-benzisothiazolin-3-one with alkylating agents such as methyl iodide and dimethyl sulfate is known. For example, A. Reissert & E. Manus, *Chem. Ber.*, (1928), vol. 61, pp. 1308-1316, disclose methylation of 1,2-benzisothiazolin-3-one with methyl iodide. However, this reaction produces mostly the O-alkylation product rather than 2-alkyl-1,2-benzisothiazolin-3-one. There is a need for a more effective preparation of 2-alkyl-1,2-benzisothiazolin-3-ones from 1,2-benzisothiazolin-3-one.

The problem addressed by this invention is to provide an improved preparation of 2-alkyl-1,2-benzisothiazolin-3-ones from 1,2-benzisothiazolin-3-one.

STATEMENT OF THE INVENTION

The present invention is directed to a method for preparation of 2-alkyl-1,2-benzisothiazolin-3-ones from 1,2-benzisothiazolin-3-one; said method comprising contacting 1,2-benzisothiazolin-3-one with a dialkyl carbonate in the presence of a base.

DETAILED DESCRIPTION OF THE INVENTION

"BIT" is 1,2-benzisothiazolin-3-one. "MBIT" is 2-methyl-1,2-benzisothiazolin-3-one. "BBIT" is 2-n-butyl-1,2-benzisothiazolin-3-one. Unless otherwise specified, temperatures are in degrees centigrade (° C.), references to percentages are percentages by weight (wt %) and amounts and ratios are on a weigh basis. An "alkyl" group is a hydrocarbyl group having from one to twenty-two carbon atoms in a linear, branched or cyclic arrangement, preferably from one to eight carbon atoms, preferably from one to four carbon atoms. Preferably, alkyl groups are linear or branched, preferably linear.

Preferably, the peak temperature of the reaction mixture is no greater than 210° C., preferably no greater than 200° C., preferably no greater than 190° C., preferably no greater than 180° C., preferably no greater than 170° C., preferably no greater than 165° C., preferably no greater than 160° C., preferably no greater than 155° C., preferably no greater than 150° C.; preferably the peak temperature of the reaction mixture is at least 125° C., preferably at least 135° C., preferably at least 140° C., preferably at least 145° C.

Preferably, the base is a metal or ammonium carbonate, metal hydroxide, metal hydride, metal oxide, alkali metal alkoxycarbonate (i.e., alkoxycarbonic acid, alkali metal salt), metal alkoxide or a hindered amine base (e.g., 1,5-diazabicyclo[4.3.0]non-5-ene (DBN) 1,8-diazabicyclo[5.4.0]undec-7-ene (DBU) and N,N-diisopropylethylamine); preferably an alkali metal carbonate, alkali metal hydroxide, alkali metal alkoxycarbonate, alkali metal alkoxide or magnesium methoxide; preferably sodium, lithium or potassium carbonate, sodium methoxide or magnesium methoxide; preferably sodium or potassium carbonate; preferably sodium carbonate, preferably potassium carbonate. Preferably, the ratio of moles of base to moles of BIT is at least 0.01/1, preferably at least 0.02/1, preferably at least 0.03/1, preferably at least 0.04:1, preferably at least 0.05/1; preferably no greater than 2/1, preferably no greater than 1.5/1, preferably no greater than 1/1, preferably no greater than 0.7/1, preferably no greater than 0.5/1, preferably no greater than 0.3/1, preferably no greater than 0.2/1, preferably no greater than 0.15/1, preferably no greater than 0.1/1.

Preferably, the dialkyl carbonate has $C_1$-$C_4$ alkyl groups, preferably $C_1$-$C_3$ alkyl groups; preferably the dialkyl carbonate is dimethyl carbonate. Preferably, the two alkyl groups are the same. Preferably, the dialkyl carbonate has primary alkyl groups, preferably primary $C_1$-$C_4$ alkyl groups (e.g., methyl, ethyl, n-propyl, n-butyl, isobutyl); preferably methyl, ethyl, n-propyl or n-butyl; preferably methyl, ethyl or n-propyl; preferably methyl. Preferably, the weight ratio of dialkyl carbonate to BIT is at least 1.5/1, preferably at least 3/1, preferably at least 5/1, preferably at least 7/1, preferably at least 9/1. The maximum amount of dialkyl carbonate is not believed to be critical and the dialkyl carbonate may also function as the solvent; however, for economic reasons, preferably the maximum weight ratio of dialkyl carbonate to BIT is no greater than 20/1, preferably no greater than 15/1, preferably no greater than 12/1.

Preferably, the reaction is carried out without solvent, i.e., with the reaction mixture containing only BIT, dialkyl carbonate and a base. If a solvent is used (other than the dialkyl carbonate), preferred solvents include, e.g., acetonitrile and other polar aprotic solvents (e.g., N,N-dimethylformamide), aliphatic hydrocarbons (e.g., hexane and isooctane), aromatic hydrocarbons (e.g., toluene and xylenes) and ethers (e.g., polyethylene glycols, glymes, dibutyl ether, crown ethers).

Commercially available BIT may contain up to 15% water. Preferably, to avoid decomposing the dialkyl carbonate, the wet BIT is dried to remove most of the water prior to contacting it with the dialkyl carbonate. Drying can be accomplished by known techniques, e.g., oven drying or azeotropic drying with solvents.

The reaction time may be determined by the usual known methods, e.g., taking samples for analysis to determine completeness of alkylation, and will of course depend on the temperature and the exact nature of the reactants. In general, it is preferred that the reaction time is at least 2 hours, preferably at least 3 hours, preferably at least 4 hours, preferably at least 5 hours, preferably at least 6 hours. The upper bound on the reaction time is not critical, but for practical reasons it is preferred that it not exceed 24 hours, preferably 18 hours, preferably 12 hours.

Preferably, methanol is removed from the reaction mixture during the reaction. After the reaction, preferably the reaction mixture is filtered to remove solids. If a solvent was used, the product may be separated by crystallization or distillation.

The most preferred 2-alkyl-1,2-benzisothiazolin-3-ones from a commercial standpoint are MBIT and BBIT; these are the products of alkylation on the nitrogen atom of BIT ("N-alkylation") by dimethyl carbonate or di-n-butyl carbonate, respectively. The 2-alkoxy-1,2-benzisothiazoles are the undesired byproducts resulting from alkylation on the carbonyl oxygen atom of BIT ("O-alkylation"). Separation of the N-alkyl product from the O-alkyl product may be achieved using standard techniques for separation of organic compounds, e.g., crystallization, distillation and extraction.

EXAMPLES

Example 1

To a 300 mL 316 stainless steel PARR reactor equipped with a magnetic drive over head stirring motor, pressure gauge, depressurization vent line, and heating mantle was added 15.05 g of dry 1,2-benzisothiazol-3(2H)-one (BIT), 0.34 g of potassium carbonate, and 150 mL of dimethyl carbonate. The reactor assembly was sealed and over the next 7 hours heat was applied with a peak internal temperature of 158° C. being reached. The reactor assembly was allowed to cool overnight and was vented to relieve residual pressure before opening. The reactor contained a light brown liquid with a small amount of solids which were removed by filtration. Analysis of this liquid (157.09 g) found it to contain 9.9% 2-methyl-1,2-benzisolthiazol-3-(2H)-one (MBIT) and 0.9% 3-methoxy-1,2-benzisothiazole (MOBIT). The product selectivity was calculated to be 91.5% MBIT and 8.5% MOBIT or approximately 10.8:1 favoring N-methylation relative to O-methylation.

Example 2

Example 1 was repeated, except that the peak internal reaction temperature was limited to 143° C. In this case the reaction the reaction was incomplete as determined by the presence of unreacted BIT which as removed via filtration. Analysis of the filtrate (173.04 g) found it to contain 3.3% MBIT and 0.2% MOBIT. The product selectivity was calculated to be 94.3% MBIT and 5.7% MOBIT, or approximately 16.5:1 favoring N-methylation.

Example 3

In a manner similar to example 1, this was repeated except that the peak internal reaction temperature was allowed to reach 162° C. The reactor contained a brown liquid with a small amount of solids which were removed by filtration. Analysis of this liquid (181.91 g) found it to contain 10.5% 2-methyl-1,2-benzisothiazol-3-(2H)-one (MBIT) and 1.0% 3-methoxy-1,2-benzisothiazole (MOBIT). The product selectivity was calculated to be 91.3% MBIT and 8.7% MOBIT or approximately 10.5:1 favoring N-methylation.

Example 4

To a 15 mL round bottom flask equipped with a magnetic stir bar, reflux condenser and heating mantle was added 0.56 g dry BIT, 0.10 g potassium carbonate and 4.86 g of dipropyl carbonate. The resulting mixture was heated and maintained at reflux (ca. 150° C.) for 6 hours. After cooling to room temperature the resulting slurry was filtered with the aid of a small volume of ethyl acetate. The resulting filtrate was concentrated to remove the extra solvent and then the solution was analyzed by HPLC. Analysis of this liquid found it to contain 8.2% 2-n-propyl-1,2-benzisolthiazol-3-(2H)-one (PBIT) and 1.3% 3-n-propoxy-1,2-benzisothiazole (POBIT). The product selectivity was thus calculated to be 86.3% PBIT and 13.7% POBIT or approximately 6.3:1 favoring N-alkylation.

Comparative Example 1

To a 100 mL 3 neck round bottom flask equipped with a thermometer, magnetic stirring bar and pressure equalizing addition funnel was added 3.90 g potassium carbonate, 4.25 g of dried 1,2-benzisothiazol-3(2H)-one along with 50 mL of anhydrous acetonitrile. Stirring was initiated and the reaction was kept at room temperature. The sandy slurry became more flocculent over time. Over approximately 90 minutes, 2.9 mL of dimethyl sulfate was slowly added dropwise to the mixture. The reaction mixture thinned considerably over time and after holding for 30 minutes after the end of the dimethyl sulfate addition, 1 mL of water was added. The mixture was filtered and the liquid phase was concentrated to afford an oily residue. This material was partitioned between ethyl acetate and saturated sodium chloride solution to which a small amount of NaOH was added to destroy any remaining dimethyl sulfate. The layers were separated and upper organic layer was washed with a second volume of saturated sodium chloride solution (no added NaOH), separated, dried over anhydrous magnesium sulfate, and concentrated under vacuum to afford 4.87 grams of a light tan oil.

Analysis of this material found it to contain 65.7% MBIT and 26.3% MOBIT, a calculated N/O-methylation ratio of only 2.5:1.

Summary of Examples

| | alkyl group | alkylating agent | peak temperature, ° C. | solvent | N/O alkylation |
|---|---|---|---|---|---|
| Ex. 1 | methyl | dimethyl carbonate | 158 | none | 10.8/1 |
| Ex. 2 | methyl | dimethyl carbonate | 143 | none | 16.5/1 |
| Ex. 3 | methyl | dimethyl carbonate | 162 | none | 10.5/1 |
| Ex. 4 | n-propyl | dipropyl carbonate | 150 | none | 6.3/1 |
| C. Ex. 1 | methyl | dimethyl sulfate | room temp. | acetonitrile | 2.5/1 |

The invention claimed is:

1. A method for preparation of 2-alkyl-1,2-benzisothiazolin-3-ones from 1,2-benzisothiazolin-3-one; said method comprising contacting 1,2-benzisothiazolin-3-one with a dialkyl carbonate and a base.

2. The method of claim 1 in which the dialkyl carbonate has primary alkyl groups.

3. The method of claim 2 in which the base is an alkali metal carbonate, alkali metal hydroxide, alkali metal alkoxycarbonate, alkali metal alkoxide or magnesium methoxide.

4. The method of claim 3 in which the dialkyl carbonate has primary $C_1$-$C_4$ alkyl groups.

5. The method of claim 4 in which the peak reaction temperature is from 140° C. to 180° C.

6. The method of claim 5 in which a ratio of moles of the base to moles of 1,2-benzisothiazolin-3-one is from 0.02/1 to 0.5/1.

7. The method of claim 6 in which a weight ratio of dialkyl carbonate to 1,2-benzisothiazolin-3-one is from 3/1 to 15/1.

8. The method of claim 7 in which the dialkyl carbonate is dimethyl carbonate.

9. The method of claim 8 in which the base is sodium or potassium carbonate.

10. The method of claim 9 in which the peak reaction temperature is from 145° C. to 170° C.

* * * * *